(12) United States Patent
Proksa et al.

(10) Patent No.: US 6,269,141 B1
(45) Date of Patent: Jul. 31, 2001

(54) COMPUTER TOMOGRAPHY APPARATUS WITH A CONICAL RADIATION BEAM AND A HELICAL SCANNING TRAJECTORY

(75) Inventors: Roland Proksa, Hamburg (DE); Jan Timmer, Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/368,850

(22) Filed: Aug. 5, 1999

(30) Foreign Application Priority Data

Aug. 5, 1998 (DE) ............................................. 198 35 296

(51) Int. Cl.[7] ........................................................ A61B 6/00
(52) U.S. Cl. .................................... 378/19; 378/4
(58) Field of Search ..................... 378/19, 4, 907

(56) References Cited

U.S. PATENT DOCUMENTS 5,291,402 * 3/1994 Pfoh .
5,335,255 * 8/1994 Seppi et al. ............................... 378/4
5,473,658 * 12/1995 Wallschlaeger .......................... 378/15
5,963,614 * 10/1999 Hu et al. ................................. 378/15

OTHER PUBLICATIONS

"Exact cone beam CT with a spiral scan" by K.C.Tam, S. Samarasekera and F. Sauer. In Phys. Med. Biol. 43(1998) pp. 1015–1024.

* cited by examiner

*Primary Examiner*—David V. Bruce
*Assistant Examiner*—Pamela R. Hobden
(74) *Attorney, Agent, or Firm*—John F. Vodopia (57) ABSTRACT

The invention relates to a computer tomography apparatus in which the scanning trajectory is shaped as a helix and a conical radiation beam traverses the examination zone. According to the invention, the dimension of the detector window (or the part thereof which is used for the reconstruction) is a factor of 3, 5, 7 . . . larger than the distance between neighboring turns of the helix. Using this geometry, each voxel in the examination zone is irradiated exactly from an angular range of $3\pi, 5\pi, 7\pi$ . . . when it traverses the cone beam. Such data acquisition yields an improved image quality.

6 Claims, 6 Drawing Sheets

COMPUTER TOMOGRAPHY APPARATUS WITH A CONICAL RADIATION BEAM AND A HELICAL SCANNING TRAJECTORY

BACKGROUND OF THE INVENTION

The invention relates to a computer tomography apparatus which includes a scanning unit which includes a radiation source and a detector unit which is connected thereto in order to detect a conical radiation beam, emitted by the radiation source, after its passage through an examination zone or an object present therein, a drive device for producing a relative motion in the form of a helix, consisting of a rotation about an axis of rotation and an advance in the direction parallel to the axis of rotation, between the scanning unit and the examination zone or the object, and a reconstruction unit for reconstructing the spatial distribution of the absorption within the examination zone from the measuring data acquired by the detector unit within a detector window defined by the helix.

A computer tomography apparatus of this kind (also referred to as CT apparatus hereinafter) is known from the PCT application SE 98/00029, dated Jan. 14, 1998. For the reconstruction of the absorption distribution the known computer tomography apparatus takes into account only the measuring data which is present within a detector window which is defined in the direction of the z axis by the projection of two successive turns of the helix (in this context and hereinafter a detector window is to be understood to mean the part of the measuring surface of the detector unit which acquires exclusively the data required for the reconstruction). It can be demonstrated that when the detector window is configured in this manner, the radiation source projects each voxel in the examination zone, upon its entry into and its departure from the radiation beam, onto the detector window from exactly 180° offset positions (relative to the respective voxel). The measuring data thus acquired enables exact reconstruction of the absorption distribution in the examination zone, even when the object present therein is longer than the part of the examination zone which is covered by the conical radiation beam.

OBJECTS AND SUMMARY OF THE INVENTION

It is an object of the present invention to improve a computer tomography of the kind set forth even further. This object is achieved according to the invention in that the connecting lines from the radiation source to the two edges of the detector window, being mutually offset in the direction of the axis of rotation, intersect two segments of the helix which are offset by the distance $(2n+1)p$ in the direction of the axis of rotation, where n is an integer number $\geq 1$ and p corresponds to the axial offset between two neighboring turns of the helix.

Whereas in the known computer tomography apparatus the two edges of the detector window are situated at a distance from one another which corresponds to the projection of two neighboring detector turns on the detector unit, according to the invention this distance amounts to an odd multiple thereof. As a result, when the projection of a point in the examination zone has moved from one edge of the window to the other edge, the radiation source will have rotated exactly through an angle $(2n+1)\pi$ about this point. In this case no redundant measuring data is obtained either. All measuring data acquired within the detector window can be used for the reconstruction.

Because of the fact that the radiation source rotates through an odd multiple about the individual points of the examination zone, the sensitivity of the method to data inconsistency (resulting from motion of the object to be examined during the scanning) is less than in the known method. This is so even though the signal-to-noise ratio, averaged across the entire examination zone, in principle is not worse than during the acquisition of the measuring data by means of the known computer tomography apparatus (provided that the speed of advancement and the intensity of the radiation source are the same in both cases).

However, in comparison with the known computer tomography apparatus the signal-to-noise ratio at individual points is more uniformly distributed across the examination zone, because the location-dependent fluctuation of the periods of time during which a point is projected onto the detector window is less severe. In the known computer tomography apparatus a variation of the projection duration of 2:1 occurs when the radius of the object cylinder, within which an object can be completely covered by the conical radiation beam, amounts to half the radius of the trajectory of the radiation source about the axis of rotation. For the same geometry in an apparatus according to the invention this variation amounts to only 1.25:1 (for $n=1$) or 1.14:1 (for $n=2$). The artefacts accompanying this variation are thus substantially reduced by the invention.

The detector window according to the invention can be realized by shaping the detector unit and/or the conical radiation beam formed by a collimator accordingly. When the detector unit describes an arc of circle around the axis of rotation, the development of the detector window should have the shape of a parallelogram; a distorted parallelogram would be required if the detector unit were to define (in a plane perpendicular to the axis of rotation) an arc of circle about the radiation source. The realization of detector units with such shapes of the development is intricate.

However, use can also be made of a detector unit whose development is shaped as a rectangle, provided that this rectangle is configured to be so large in the direction of the axis of rotation that it encloses the development of the detector window. Such a rectangular detector, therefore, must be larger than the desired detector window. In accordance with the invention the ratio of the required detector surface to the actual detector surface, however, is more favorable than for the detector window of the known CT apparatus.

A preferred embodiment is disclosed in claim 2. In that case the distance between the edges of the detector window thus amounts to three times the distance between two turns of the helix.

Claim 3 describes a preferred embodiment. The advantages thus achieved are analogous to those which occur in conventional computer tomography apparatus in which only a single detector row is included and the center of the detector elements and the puncture point of a line intersecting the axis of rotation are mutually offset by one quarter of the detector width; after half a rotation of the scanning unit, the detector unit has been displaced by one half detector width in the line direction. Therefore, the same data is not measured twice but in intermediate positions; the measuring data is thus more attractively distributed and the image quality is enhanced. Such an offset is not possible in the known computer tomography apparatus.

Similar effects are also obtained in the direction of the axis of rotation in the embodiment described in claim 4.

The embodiment of the invention as defined in claim 5 enables a choice between a (first) mode of operation, in which the radiation source rotates through the angle $\pi$ about each examination point during its passage through the radiation cone, and a (second) mode of operation in which this rotation amounts to $(2n+1)\pi$. When the same rotary speed is used for both modes of operation, in the case of the same detector dimensions the scanning speed in the first mode of operation is a factor $2n+1$ higher than in the second mode of operation in which, however, the signal-to-noise ratio or the image quality is better. The user can thus select the mode of operation which is most attractive for the relevant examination.

Claim 6 discloses a preferred embodiment for the reconstruction of the absorption distribution in the examination zone from the measuring data acquired within the detector window. The absorption distribution can also be reconstructed from the measuring data in a different manner, but the described means enable particularly simple reconstruction steps and a particularly high quality of the reconstruction or a particularly high image quality.

BRIEF DESCRIPTION OF THE DRAWINGS

The invention will be described in detail hereinafter with reference to the drawings. Therein.

DESCRIPTION OF THE PREFERRED EMBODIMENTS

Figure 1:
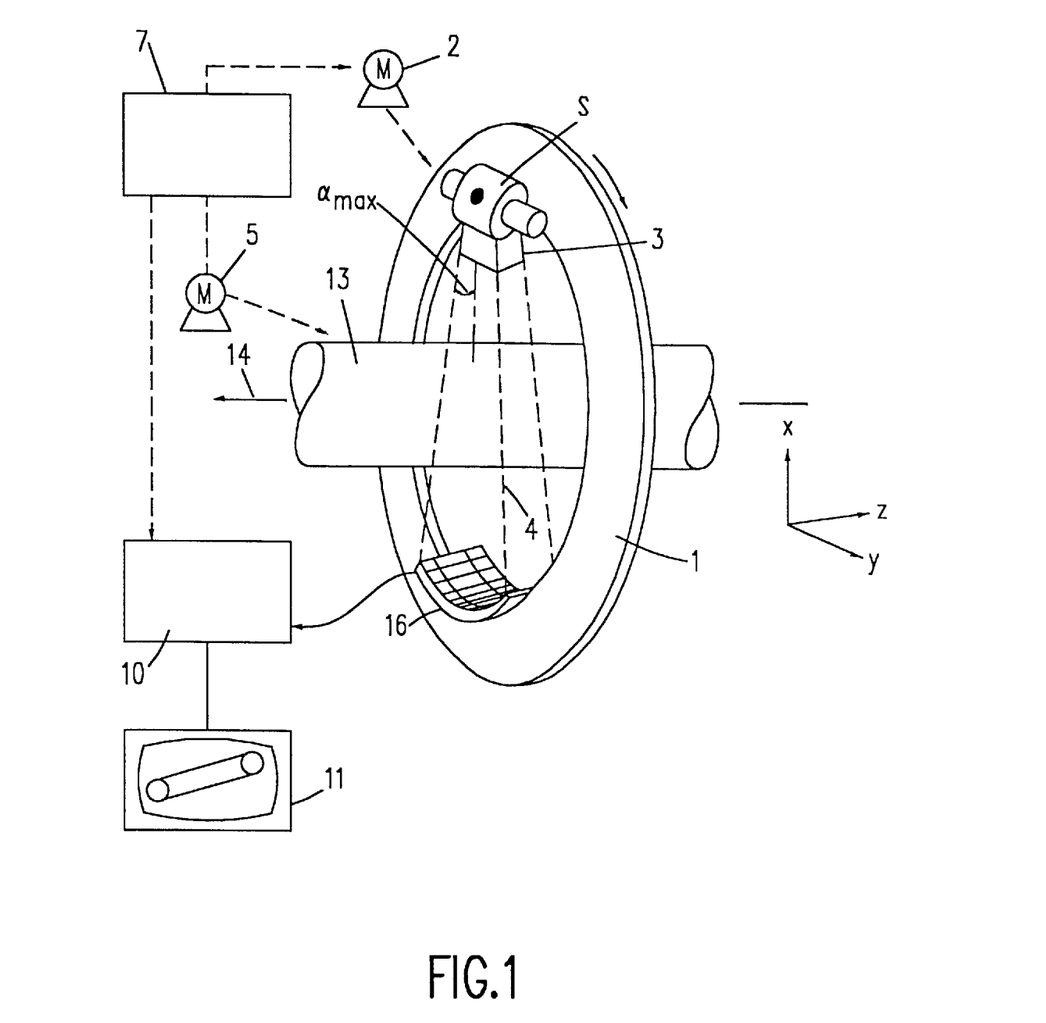
FIG. 1 is a diagrammatic representation of a computer tomography apparatus according to the invention.

The computer tomography apparatus shown in FIG. 1 includes a gantry 1 which is capable of rotation about an axis of rotation 14 which extends parallel to the z direction. To this end, the gantry is driven at a preferably constant, but adjustable angular speed by a motor 2. A radiation source S, for example an X-ray tube, is mounted on the gantry. The X-ray source is provided with a collimator device 3 which forms a conical radiation beam 4 from the radiation produced by the radiation source S, i.e. a radiation beam which has a finite dimension other than zero in the direction of the z axis as well as in a direction perpendicular thereto (i.e. in the x-y plane of the co-ordinate system shown in FIG. 1).

The radiation beam 4 traverses an object (not shown) which is present in an examination zone 13. The examination zone 13 is shaped as a cylinder which will also be referred to as the object cylinder hereinafter. After having traversed the object cylinder 13, the X-ray beam 4 is incident on a two-dimensional detector unit 16 which is mounted on the gantry 1 and includes a number of detector rows, each of which includes a plurality of detector elements. Each detector element detects a ray from the radiation beam 4 in each radiation source position. The detector unit 16 may be arranged on an arc of circle about the axis of rotation 14, but other detector geometries are also feasible; for example, it may be arranged on an arc of circle around the radiation source S.

The angle of aperture $\alpha_{max}$ of the radiation beam 4 (the angle of aperture is defined as the angle enclosed by a ray of the beam 4 which is situated at the edge in the x-y plane relative to a plane defined by the radiation source S and the axis of rotation 14) then determines the diameter of the object cylinder 13 within which the object to be examined must be present during the acquisition of the measuring values. The examination zone 13, or an object present therein, for example a patient accommodated on a patient table, can be displaced parallel to the direction of the axis of rotation 14, or the z axis, by means of a motor 5. The speed of such displacement in the z direction is constant and preferably adjustable.

The measuring data acquired by the detector unit 16 is applied to an image processing computer 10 which reconstructs therefrom the absorption distribution in the part of the examination zone 13 which is irradiated by the radiation cone 4 in order to display it, for example on a monitor 11. The motors 2 and 5, the image processing computer 10, the radiation source S and the transfer of the measuring data from the detector unit 16 to the image processing computer 10 are controlled by a suitable control unit 7.

When the motor 5 stands still and the motor 2 rotates the gantry, a circular scanning motion of the radiation source S and the detector unit occurs. The control unit 7, however, can also control the motors 2 and 5 in such a manner that the ratio of the speed of advancement v of the examination zone 13 to the angular velocity o of the gantry is constant. In this case the radiation source S and the examination zone move relative to one another along a helical trajectory. Only this helical scanning motion will be considered hereinafter. In the case of a helical scanning motion it is in principle irrelevant whether the scanning unit S, 16 or the examination zone 13 performs the rotary or the advance motion; only the relative motion is of importance.

Figure 2:
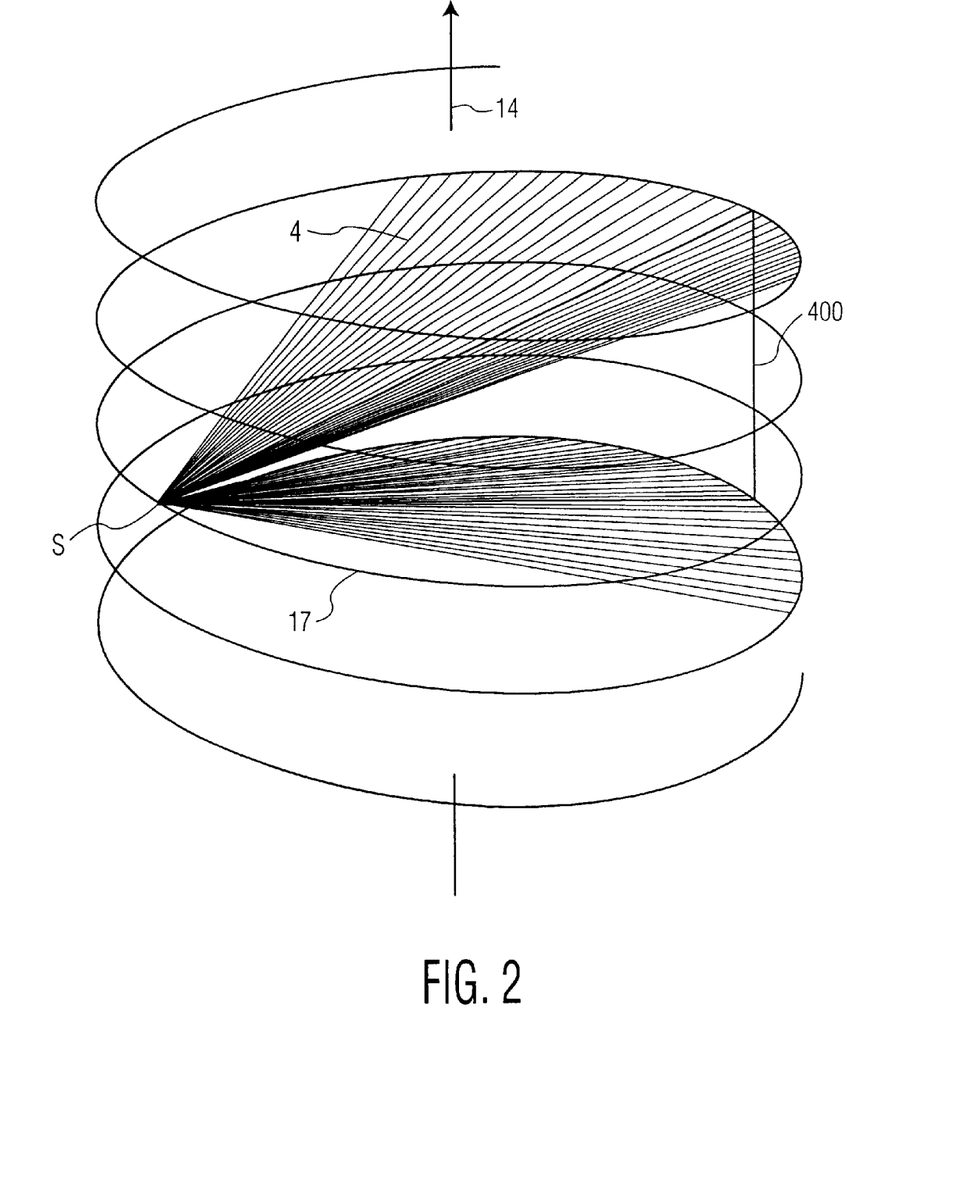
FIG. 2 shows the helical scanning trajectory described relative to one another by the scanning unit and an object present in the examination zone.

Therefore, in FIG. 2 it is assumed that the radiation source S (and the detector unit 16 which is connected thereto, via the gantry, and not shown in FIG. 2) moves along the helical trajectory 17, whereas the examination zone 13 (which, like the object situated therein, is not shown in FIG. 2) is stationary. The conical radiation beam 4 emitted by the radiation source S is incident on the detector unit 16 which is situated to the other side of the examination zone and whose center coincides with a central ray which is emitted by the radiation source S and intersects the axis of rotation 14 perpendicularly. The radiation beam emanating from the radiation source 4 may be considered to be composed of a plurality of fan-shaped beams which are situated in planes which extend parallel to the axis of rotation 14 and intersect in the radiation source S. Even though this radiation beam also contains rays which are grouped in a fan-shaped manner in other planes, hereinafter only combinations of rays which are situated in a plane parallel to the axis of rotation 14, like the fan-shaped beam 400, will be referred to as fan-shaped beams. The measuring data of each individual fan-shaped beam can be acquired by a column of detector elements of the detector unit which extends parallel to the axis of rotation 14.

The angle of aperture $\alpha_{max}$ of the radiation beam 4 (in a plane which contains the radiation source S and extends perpendicularly to the axis of rotation 14) is proportioned so that its outer fan-shaped beams are exactly tangent to the object cylinder 13. If $\alpha_{max}=30°$, the radius of the object cylinder amounts to exactly half the radius R of the helical trajectory 17. The aperture of the collimator device 3 is shaped so that two turns of the helix 17, which face the radiation source and are offset by the distance 3p relative to one another (p corresponds to the advance in the z direction during one complete revolution of the radiation source S) are coincident with the rays at the upper and the lower edge (in the rendition of FIG. 2) of the radiation beam 4.

The upper and the lower edge of the detector window according to the invention are coincident with the projection of the turns of the helix (or the segments thereof which face the radiation source) on the detector unit, i.e. the connecting lines from the radiation source to said edges intersect said turns. This also holds when the detector window is not situated on an arc of circle, defined by the helix, about the axis of rotation but, for example on an arc of circle about the radiation source S; the latter offers special advantages. In that case the detector window no longer has the shape of a regular parallelogram as shown in FIG. 3, but constitutes a distorted parallelogram whose upper and lower sides are curved.

Figure 3:
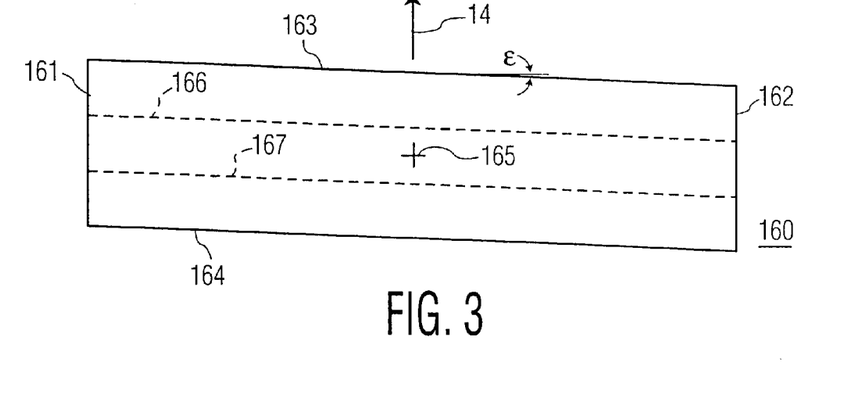
FIG. 3 shows a development of the detector unit.

FIG. 3 shows the development of the detector window 160 from the cylinder defined by the helix 17 into the plane of drawing. The development has the shape of a parallelogram having sides 161, 162 extending parallel to the z direction (the distance therebetween is larger as the angle of aperture $\alpha_{max}$ of the radiation beam is larger). For the length of these sides, i.e. the height h of the detector window, it holds that h=3p. The upper edge 163 and the lower edge 164 of the detector window enclose an angle E relative to the perpendicular to the axis of rotation 14, which angle can be calculated in conformity with the relation $\tan\epsilon=p/2\pi R$, where R is the distance between the radiation source and the axis of rotation. In this respect it is assumed that the speed of advancement and the rotary speed are constant. FIG. 3 also shows the center 165 of the detector window and the dashed lines 166 and 167 represent the projection of the two turns which are situated between the turns of the helix which coincide with the upper edge 163 and the lower edge 164.

Each point in the examination zone is projected onto the lower edge 164 upon entering the conical radiation beam 4 and onto the upper edge 163 upon leaving the radiation beam. It can be demonstrated that the radiation source performs a rotation of exactly $3\pi$ about the relevant point while its projection travels from the lower edge 164 of the detector window to the upper edge 163. In relation to the axis of rotation, however, the rotary motion performed by the radiation source may be larger or smaller than $3\pi$.

Figure 4:
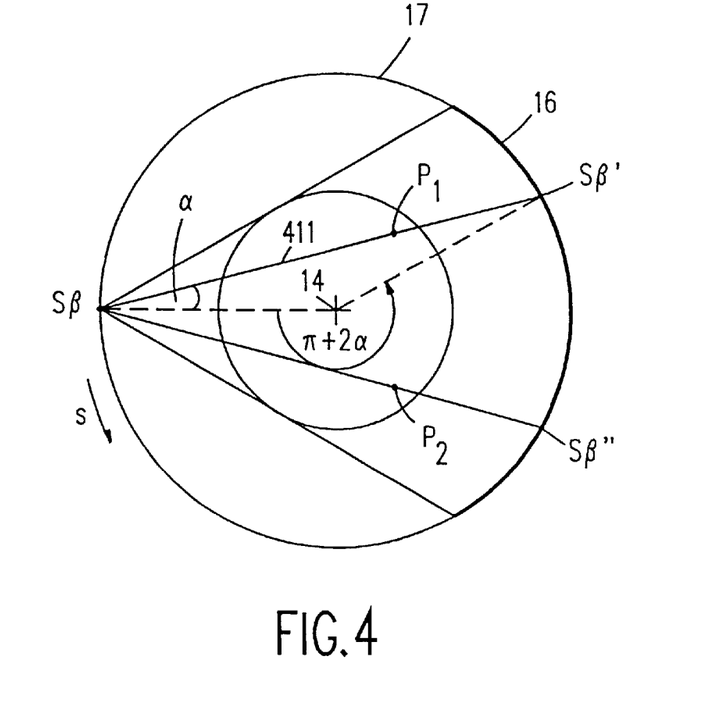
FIG. 4 shows the geometrical ratios, viewed in the direction of the axis of rotation.

This is illustrated in FIG. 4 which shows the geometrical ratios in a view parallel to the z axis or the axis of rotation 14. The helix 17 then becomes a circle and the axis of rotation 14 becomes a point, being the center of the circle. The radiation source moves along the trajectory 17 in the direction of the arrow s and the Figure shows a ray 411 which irradiates a point $P_1$ at the instant at which it enters the radiation cone. After the radiation source has completed a full revolution from its position $S_\beta$ and has additionally been rotated through the angle $\pi+2\alpha$ (so overall through the angle $3\pi+\alpha$), it is situated in a position $S_\beta$ in which the projection of the upper point $P_1$ passes exactly the upper edge 163 of the detector window and which, in relation to the point $P_1$, has been rotated exactly through $3\pi$ (with respect to the initial position of the radiation source).

On the other hand there is shown a point $P_2$ for which, upon its entry into the radiation beam, the radiation source is also situated in the position $S_\beta$, but occupies the position $S_\beta"$ upon its departure. The radiation source has again been rotated through exactly $3\pi$ about the point $P_2$, but only through the angle $3\pi-2\alpha$ (about the axis of rotation.

Therefore, the point $P_1$ is present in the conical radiation beam for a period of time which is longer in proportion to the rotary angle ($3\pi+2\alpha$) than the period of time during which the point $P_2$ (with the rotary angle $3\pi-2\alpha$) is present therein. The ratio of these radiation periods, correlated to the signal-to-noise ratio for the relevant point, is 1.25:1 in the worst case (for $\alpha=\alpha_{max}=30°$). If the radiation source, however, were rotated only through the angle $\pi$ bout the points $P_1$ or $P_2$ (as in the above-mentioned known computer tomography apparatus), this ratio would be 2:1, implying a substantially greater location-dependency of the signal-to-noise ratio.

Figure 5:
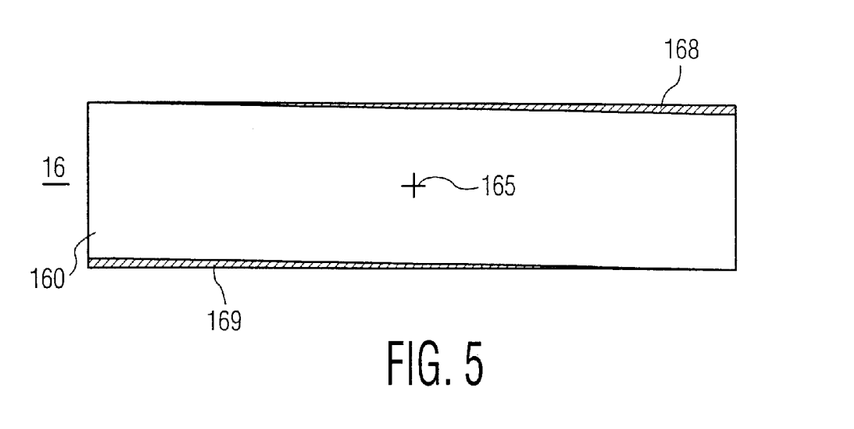
FIG. 5 shows another detector unit in a first mode of operation.

The development of the detector window 160 shown in FIG. 3 has a given drawback in that it deviates from the customary rectangular shape. This deviation is even more pronounced when the detector unit is arranged on a circular cylinder whose cylinder axis extends through the radiation source S and even more so if use is made of a flat detector unit. Therefore, FIG. 5 shows a detector unit whose development corresponds to a rectangle and whose dimensions in the z direction are chosen to be such that they enclose at least the detector window 160. In that case the areas 168, 169, shaded in FIG. 5, remain at the upper and the lower detector edge, which areas are tapered towards the left and to the right.

There are two possibilities for achieving the desired acquisition of the measuring data (i.e. only the measuring data where each measuring point "sees" the radiation source at an angle amounting to exactly $3\pi$) despite the shape of the detector unit which deviates from the ideal shape of the detector window 160; these possibilities can also be combined:

a) the collimator 3 (FIG. 3) is constructed in such a manner that the X-rays are incident only on the detector window 160, but not on the edge areas 168, 169;

b) the reconstruction is performed exclusively on the basis of the measuring values from detector elements situated within the detector window 160. The measuring values from all detector elements situated within the areas 168 and 169 are ignored. Because the position of the detector window 160 relative to the detector unit 16 does not change during an examination, the amount of software required for this purpose is minimum.

The rectangle shown in FIG. 5 is larger than required to accommodate the detector window 160, i.e. a part of its detector elements is not used. This unused part can be reduced by tilting the detector unit from a first position (for a circular scanning motion), in which its symmetry axis extends parallel to the axis of rotation 14, into a second position (for a helical scanning motion) in which its symmetry axis encloses an acute angle relative to the axis of rotation 14. The upper and lower edges 168, 169 are then inclined relative to the axis of rotation in the same way as the turns of the helix.

Figure 6:
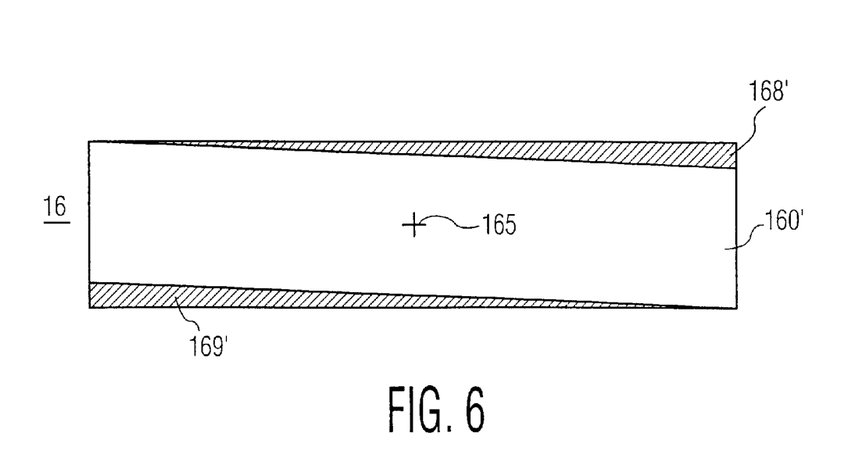
FIG. 6 shows the same detector unit in a second mode of operation.

For comparison FIG. 6 shows the development of the detector window 160' (or the detector unit 16) used in the previously mentioned known CT apparatus, using the same, rectangular detector unit 16 as shown in FIG. 5. It appears that the slope of the upper and the lower edge of the resultant detector window 160' is a factor of approximately 3 larger than in the FIGS. 5 and 3. It also appears that the areas 168' and 169' which are required for the rectangle and contain the detector elements whose measuring values are not required for the reconstruction are wider than the areas 168, 169 in FIG. 5. Consequently, the invention uses the detector surface area more effectively.

Nevertheless, for given CT examinations it may also be useful to utilize such a detector window. To this end it would be necessary to reduce the rotary speed of the motor 2 (FIG. 1) for the rotary motion by the factor 3.

Figure 7:
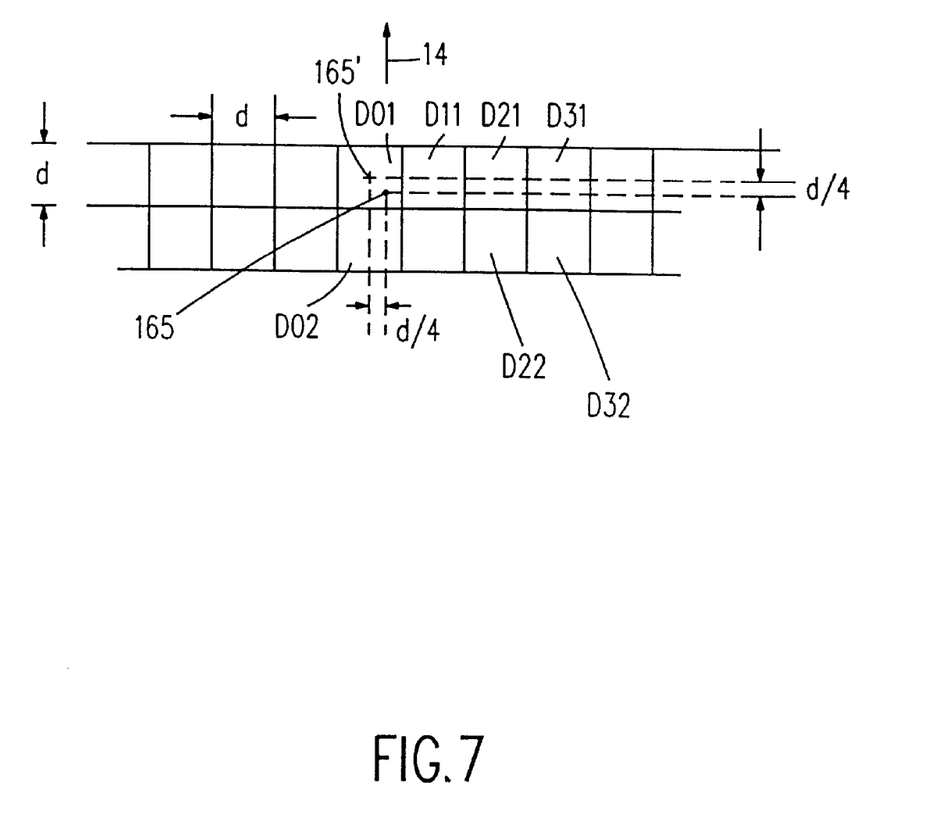
FIG. 7 shows the arrangement of individual detector elements within the detector unit.

For the above embodiment it was assumed that the edges of the detector window, mutually offset in the direction of rotation, are defined by the turns of two segments of the helix which are offset by the distance 3p in the z direction. This offset, however, may also amount to 5p, 7p, 9p (generally speaking, (2n+1)p, where n>1). The signal-to-noise ratio is then even less dependent on the location and in the case of a detector with a rectangular development of the active detector surface an even larger part thereof is used. However, the rotary speed (or the ratio of rotary speed to transport speed) must then be 5/3, 7/3, 9/3 or (2n+1)/3 higher. FIG. 7 shows an attractive embodiment of the detector unit 16. The Figure shows two rows of detector elements $D_{01} \ldots D_{31}$ and $D_{02} \ldots D_{32}$. The detector element $D_{01}$ is situated in the central row and in the central column. Its center 165', however, does not coincide with the center 165 of the detector window which is defined by the point of puncture of a line which emanates from the radiation source S and intersects the axis of rotation 14 perpendicularly. Between these two points there is an offset which amounts to d/4 in the column direction (or in the direction of the axis of rotation 14) and in the row direction, where d corresponds to the width or the length of a detector element.

As a result of this offset by d/4 in the row direction it is achieved that, after one half revolution of the scanning unit S, 16, measurement does not take place along the same radiation paths, but along radiation paths offset by one half width of a detector element. This offers an improved image quality. Because of the offset of the detector by d/4 in the z direction, after one half revolution the columns have also been shifted by half the width of a detector element in the z direction; this also contributes to an improved image quality.

Figure 8:
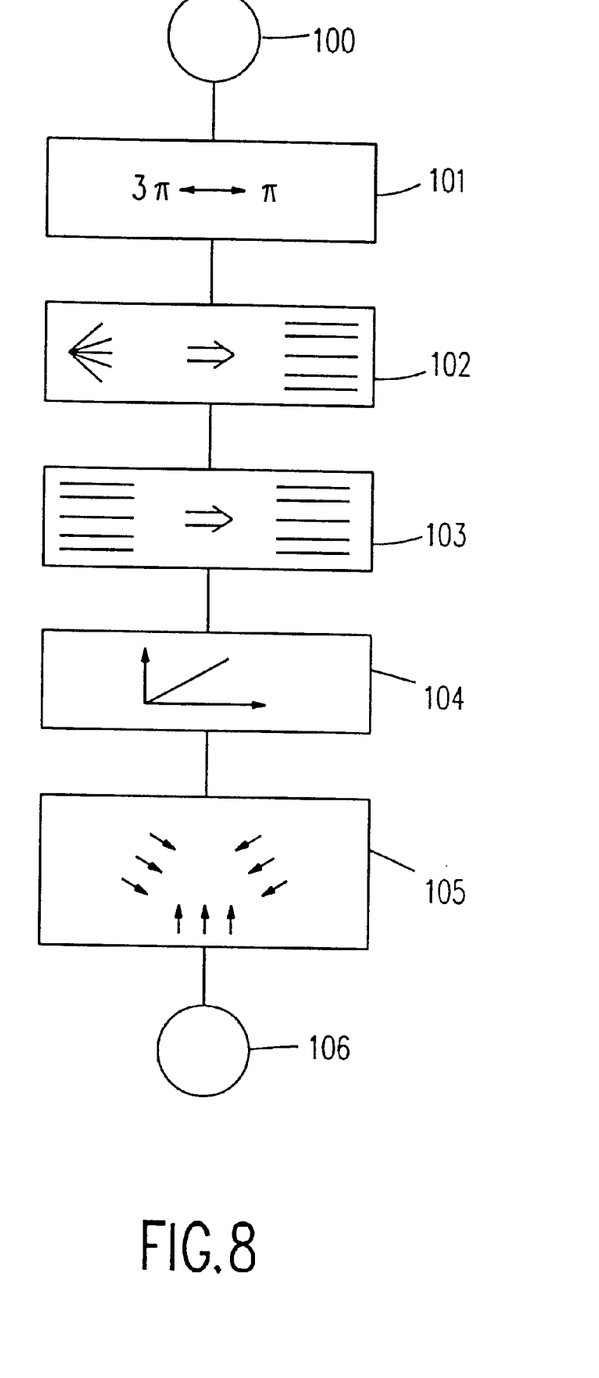
FIG. 8 shows a flow chart concerning the processing of the measuring data.

The processing of the measuring data acquired in the detector window 160 will be described in detail hereinafter on the basis of the flow chart shown in FIG. 8. It is assumed that the measuring surface of the detector unit has a rectangular shape in conformity with FIG. 5 or FIG. 6, and that the user can choose whether to use the data acquisition according to the invention, where each point in the examination zone "sees" the radiation source from an angular range of 3π (5π, 7π . . . ) during its passage through the radiation cone, or the known data acquisition as described in the preamble.

After the initialization (block 100), measuring data is acquired in block 101; the user can then specify whether the radiation source should rotate through the angle 3π (5π, 7π . . . ) or through the angle π during an advance in the z direction which corresponds to the height h of the detector window. As has been described above, this choice has a pronounced effect on the data acquisition and the quality of the reconstruction, but the actual reconstruction method need only be slightly modified. Therefore, reference is made to the description of the reconstruction method in the PCT application SE 98/00029.

Thus, first a rebinning operation is performed, during which groups of fan beams situated in parallel planes are formed during a first step 102. As has already been explained with reference to FIG. 2, the conical radiation beam can be considered to be composed of fan beams, such as the fan beam 400 in FIG. 2, which are situated in planes parallel to the axis of rotation 14. In the plan view of FIG. 4, these planes or fan beams become straight lines. Only the fan beams which are situated in planes which are parallel to one another (and parallel to the axis of rotation 14) and have been detected from different radiation source positions are combined so as to form a group (since the fan beams occurring in a single radiation source position are not parallel to one another).

Figure 9:
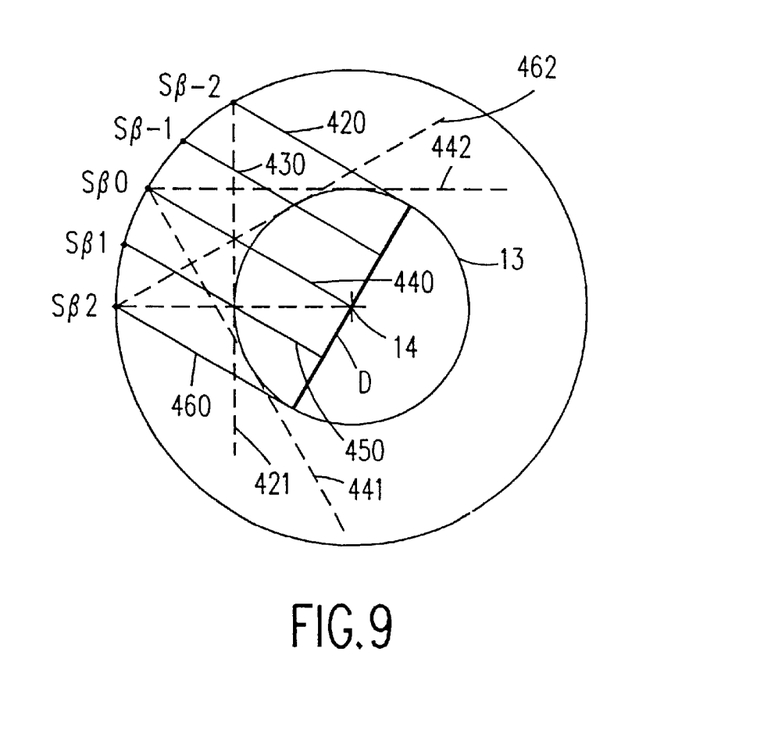
FIG. 9 shows the same view as FIG. 4, be it after partial rebinning.

FIG. 9 shows a single group of such fan beams; therein, the plane of drawing perpendicularly intersects the axis of rotation 14, like in FIG. 4. Successive positions of the radiation source are denoted by the references $S_{\beta-2} \ldots S_{\beta 2}$ in FIG. 9. A fan beam 420 . . . 440 . . . 460 emanates from each of these radiation source positions; this beam traverses the examination zone 13 and is situated in a plane which extends parallel to the plane defined by the central detector position $S_{\beta 0}$ and the axis of rotation 14. For fan beams belonging to the same group it holds that the sum of the fan angle α (being the angle enclosed by the plane of the fan beam relative to the plane defined by the associated radiation source position and the axis of rotation 14) and the angle enclosed by the radiation source relative to the axis of rotation 14 is constant. If no fan beam exactly satisfies this condition in a radiation source position, a fan beam situated in this plane is determined by interpolation from fan beams situated to both sides of the plane with the desired orientation and generated in the relevant radiation source position.

Also shown are a few fan beams, for example 421, 441 and 442, 462 which are situated each time at the edge of a radiation cone (and hence are tangent to the examination zone). These fan beams, however, do not belong to the group shown in FIG. 9 and, therefore, are denoted by dashed lines instead of solid lines like the fan beams belonging to the group.

FIG. 9, moreover, shows a virtual detector window D which is associated with the group shown and extends perpendicularly to the planes of the fan beams and through the axis of rotation 14. The virtual detector window D has a rectangular shape and its height is h/2 or 1.5p, the center of the virtual detector window being defined by the normal from the central radiation source position $S_{\beta 0}$ to the axis of rotation. Even though the radiation source positions $S_{\beta-2}$ and $S_{\beta 2}$ are offset relative to the central radiation source $S_{\beta 0}$ in the z direction, it can be demonstrated that the upper and lower edge rays of the fan beams 420 and 460 coincide exactly with the upper and the lower edge of the virtual detector window D. This is based on the fact that the fan beams 460 and 420, being situated to both sides of the central radiation source position $S_\beta$, are detected by columns of the real detector window 160 which are situated to the right and to the left of the center, respectively, and are situated higher and lower in the z direction, respectively, than the column which detects the fan beam emanating from $S_{\beta 0}$. Therefore, each fan beam covers one column of the virtual detector window D.

The fan beams (present in planes parallel to the axis of rotation) are assigned to a respective one of the various groups in the step 102. Ignoring the radiation source positions at the beginning and the end of the helical scanning trajectory 17, a group is formed for each radiation source position. With each group there is associated a virtual detector D whose flat rectangular surface extends perpendicularly to the planes in which the fan beams belonging to the relevant group are situated.

After all associated fan beams have been detected for at least one group in this manner, in step 103 the second part of the rebinning operation is performed, i.e. the reinterpolation or the resampling. As is shown in FIG. 9, the distance between the parallel planes in which the fan beams belonging to a group are situated decreases from the center towards the periphery. Therefore, for a regular Cartesian grid on the virtual detector window D in the step 103 the associated measuring data is determined from the measuring data assigned to the individual groups in the step 102; such determination takes place preferably by interpolation. This completes the rebinning of a parallel fan beam geometry on a rectangular surface with regularly distributed grid points, so that the subsequent processing is significantly facilitated.

Subsequently, a one-dimensional filtering operation is performed in the step 104. After the rebinning performed in the steps 102 and 103, only a single one-dimensional, location-independent filter is required for this purpose; this filter filters the measuring data in the virtual detector window D in the row direction, i.e. perpendicularly to the axis of rotation 14. This filter has an attenuation which decreases linearly as a function of the frequency. The filtering operation can in principle be performed by subjecting the measuring data yielded by the rebinning operation to a convolution with a suitable one-dimensional filter kernel.

Less work is required, however, if the filtering operation in the step 104 first includes a Fourier transformation, after which the data thus transposed to the spatial frequency domain is subjected to a ramp-like filtering operation in the row direction, after which it is transformed back to the spatial domain again by an inverse Fourier transformation.

In the step 105 the filtered data of each group or of each virtual detector window are backprojected into the examination zone again, i.e. the filtered measuring data is groupwise backprojected into the examination zone along the same radiation paths (possibly slightly modified by the step 103) along which this data has been acquired. The absorption values for the individual voxels of the examination zone result from the superposition of all (filtered) measuring data during the acquisition of which the relevant voxel was projected onto the detector window 160. For each reconstructed voxel contributions are then received from fan beams or groups from an angular range of $3\pi$ or $(2n+1)\pi$ instead of an angular range of $\pi$ as in the known method.

The reconstruction of the absorption distribution in the examination zone can thus be started already during the acquisition of the measuring data. Acquisition and reconstruction can then be performed in parallel in time until the acquisition is interrupted (at an instant which can be chosen at random) and the reconstruction is completed by means of the measuring data acquired thus far. The method is then terminated (block 106).

The absorption distribution in the examination zone can also be reconstructed in a different manner from the measuring data acquired by means of the detector according to the invention. A suitable other reconstruction method is known from Phys. Med. Biol. 43 (1998), pp. 1015–1024.

Therein, according to the so-called Grangeat method the first derivative of the surface integral is calculated from segments for each plane which intersects the object, and the partial results are accumulated in a sum. This data constitutes the first radial derivative of the Radon space which can be inverted in the object space by means of known methods. In dependence on the number of intersections between the plane to be reconstructed and the helix along which the examination zone is scanned, the following sub-cases can be distinguished for the processing of the measuring data acquired by means of the detector according to the invention:

a) no intersection.

In this case there is no information, because the plane to be reconstructed does not intersect the object.

b) one intersection.

In this case the same measuring data is acquired by the known method as well as by the invention.

c) there is an odd number of intersections.

In this case the reconstruction is performed as in the known method and the result is divided by 3 (if the detector dimension h corresponds to three times the distance of the detector turns).

What is claimed is:

1. A computer tomography apparatus which includes a scanning unit which includes a radiation source (S) and a detector unit (16) which is connected thereto in order to detect a conical radiation beam, emitted by the radiation source, after its passage through an examination zone (13) or an object present therein, a drive device (2, 5) for producing a relative motion in the form of a helix (17), consisting of a rotation about an axis of rotation (14) and an advance in the direction parallel to the axis of rotation, between the scanning unit (S, 16) and the examination zone (13) or the object, and a reconstruction unit (10) for reconstructing the spatial distribution of the absorption within the examination zone (13) from the measuring data acquired by the detector unit (16) within a detector window (160) defined by the helix (17), characterized in that the connecting lines from the radiation source (S) to the two edges (163, 164) of the detector window (160), being mutually offset in the direction of the axis of rotation (14), intersect two segments of the helix (17) which are offset by the distance $(2n+1)p$ in the direction of the axis of rotation, where n is an integer number>1 and p corresponds to the axial offset between two neighboring turns of the helix.

2. A computer tomography apparatus as claimed in claim 1, characterized in that n=1.

3. A computer tomography apparatus as claimed in claim 1, in which the detector unit (16) includes detector elements ($D_{01}$, $D_{02}$ . . . ) which are arranged in rows and columns, characterized in that the center of the rows is offset by one quarter of the width (d) of a detector element relative to a plane containing the radiation source and the axis of rotation.

4. A computer tomography apparatus as claimed in claim 1, in which the detector unit includes detector elements which are arranged in rows and columns, characterized in that the center of the columns is offset by half the width of a detector element relative to a plane containing the radiation source and extending perpendicularly to the axis of rotation.

5. A computer tomography apparatus as claimed in claim 1, characterized in that the drive device (2, 5) has two modes of operation, the ratio of the rotary speed to the transport speed being a factor $2n+1$ smaller in one operating mode in comparison with the other operating mode, so that in one operating mode each point (P1) in the examination zone (13) is irradiated by the radiation source (S) from an angular range $\pi$, whereas it is irradiated thereby from an angular range $(2n+1)\pi$ in the other mode of operation.

6. A computer tomography apparatus as claimed in claim 1, characterized in that it includes:

a) means for rebinning the measuring data so as to form a number of groups, each group including a plurality of planes which extend parallel to the axis of rotation and in which a respective fan beam is present, b) means for filtering the data of each group, formed by the rebinning, in the direction perpendicular to the axis of rotation, c) reconstruction of the spatial distribution of the absorption by backprojection of the filtered data of a plurality of groups.

* * * * *